US008968660B2

(12) United States Patent
Davis et al.

(10) Patent No.: US 8,968,660 B2
(45) Date of Patent: Mar. 3, 2015

(54) CHEMICAL ANALYZER

(75) Inventors: Stephen Charles Davis, Ascot (AU); John David Petty, Holland Park West (AU); John Thomas Huberts, Sunnybank Hills (AU)

(73) Assignee: Aqualysis Pty Ltd, Ascot (AU)

( * ) Notice: Subject to any disclaimer, the term of this patent is extended or adjusted under 35 U.S.C. 154(b) by 246 days.

(21) Appl. No.: 13/211,943

(22) Filed: Aug. 17, 2011

(65) Prior Publication Data

US 2012/0003124 A1 Jan. 5, 2012

Related U.S. Application Data

(62) Division of application No. 12/514,610, filed as application No. PCT/AU2007/001801 on Nov. 23, 2007, now abandoned.

(30) Foreign Application Priority Data

Nov. 24, 2006 (AU) ................................ 2006906573

(51) Int. Cl.
| | | |
|---|---|---|
| *G01N 21/01* | (2006.01) | |
| *G01N 21/75* | (2006.01) | |
| *G01N 31/16* | (2006.01) | |
| *G01N 35/10* | (2006.01) | |

(Continued)

(52) U.S. Cl.
CPC ................ *G01N 31/16* (2013.01); *G01N 21/01* (2013.01); *G01N 21/75* (2013.01); *G01N 2021/8411* (2013.01); *G01N 35/1002* (2013.01); *G01N 2021/0193* (2013.01); *G01N 2035/1058* (2013.01); *G01N 21/79* (2013.01)
USPC .......... 422/81; 422/68.1; 422/82.09; 436/165

(58) Field of Classification Search
CPC .................. G01N 35/1002; G01N 2035/1058; G01N 21/75; G01N 2021/0193; G01N 2021/752
USPC .......................................... 436/165
See application file for complete search history.

(56) References Cited

U.S. PATENT DOCUMENTS

| | | | |
|---|---|---|---|
| 3,469,578 A | 9/1969 | Bierman | |
| 4,318,400 A | 3/1982 | Peery et al. | |
| 4,479,989 A * | 10/1984 | Mahal | 428/35.5 |

(Continued)

FOREIGN PATENT DOCUMENTS

EP 0229982 B 7/1987

*Primary Examiner* — Yelena G Gakh
*Assistant Examiner* — Michelle Adams
(74) *Attorney, Agent, or Firm* — Novak Druce Connolly Bove + Quigg LLP

(57) ABSTRACT

A chemical analyzer analyzes a sample for a target chemical. The sample and reagent are added to a measurement cell until a detectable change is observed. A reference compound, which does not take part in the reaction between the target chemical and reagent, is added to the reagent. By measuring the concentration of the reference compound, the amount of reagent used may be determined. In one embodiment, a mechanism introduces the sample, adds reagent, mixes, cleans, and flushes the measurement cell, which incorporates a longitudinal chamber having inlets for the sample and reagent and an outlet for measured sample/reagent mixtures. A detector located in or adjacent to the chamber between the inlets and outlet and a piston movable in the chamber carries seals such that movement of a piston sequentially opens the inlets and expels the fluid. The analyzer also includes a device that delivers reagent to a measurement cell.

17 Claims, 7 Drawing Sheets

(51) Int. Cl.
  *G01N 21/79* (2006.01)
  *G01N 21/84* (2006.01)

(56) References Cited

U.S. PATENT DOCUMENTS

| 5,535,951 | A | 7/1996 | Utter |
| 6,426,230 | B1 * | 7/2002 | Feistel .......................... 436/165 |
| 2004/0115829 | A1 * | 6/2004 | Kaartinen et al. ............ 436/180 |
| 2004/0219683 | A1 | 11/2004 | Taylor et al. |
| 2006/0105465 | A1 | 5/2006 | Weber et al. |
| 2006/0222569 | A1 * | 10/2006 | Barten et al. .................. 422/100 |
| 2011/0201121 | A1 * | 8/2011 | Kaartinen ....................... 436/43 |

* cited by examiner

Page 1

CHEMICAL ANALYZER

CROSS REFERENCE TO RELATED APPLICATIONS

This application is a divisional of U.S. patent application Ser. No. 12/514,610, which is a National Phase filing under 35 U.S.C. §371 of PCT/AU2007/001801 filed Nov. 23, 2007, claiming priority to Patent Application No. 2006906573, filed in Australia on Nov. 24, 2006. The entire contents of each of the above-applications are incorporated herein by reference.

This invention relates to a method and apparatus for chemical analysis, especially analysis entailing the automatic detection of substances in solution, for example by reagent addition and titrimetry. The invention is especially suited to on-line analysis and control of chlorine content and the measurement and control of pH in pools and air conditioning towers.

BACKGROUND

Field of the Invention

The detection of substances in solution has long been determined by a variety of known techniques. A sensor such as a pH electrode may be inserted in a sample solution and the millivolts generated can be output as a pH measurement. Another known technique involves pumping a known volume or series of volumes of reagent into a defined volume of sample. The reagent and sample solutions are then mixed and a property of a component of the mixture, for example, a reaction product, is measured by a suitable detector.

As one example of the latter technique, the concentration of disinfectant such as free chlorine can be determined by the addition of a stoichiometric excess of N,N-Diethyl-p-phenylenediamine (DPD) in a suitable pH buffer:

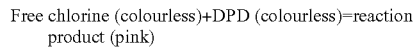
Free chlorine (colourless)+DPD (colourless)=reaction product (pink)

The concentration of the coloured reaction product can be measured by the level of absorbance of light in the green to blue range. This directly relates to the concentration of free chlorine.

As a second example of the latter technique, the pH of aqueous samples can be determined by the addition of an indicator whereby the indicator varies in colour according to the pH. The colour at a particular pH is due to the ratio of different forms of the indicator. For example the pH of swimming pool water can be ascertained by the addition of a small amount of phenol red.

The extension of the above described techniques to automated analysis especially for on-line analysis and process control has been accomplished by a number of known devices. In the case of direct sensing, a pH electrode can be connected to a measuring instrument or process controller. This has the advantages of simplicity and low cost, but suffers from the disadvantage of not being able to diagnose malfunction or fouling in real time. This is especially serious for process control, which relies on reliable measurement.

In the case of the reagent addition technique, a typical state of the art apparatus for the measurement of free chlorine by DPD is described in Hanna Instruments Volume 25 (details) page T48 Model PCA 300. This device is expensive and complex in that it contains an incoming pressure regulator, sample inlet solenoid valve, multi-channel peristaltic pump, magnetic mixer and drain valve. The device requires two reagent containers which are open to the atmosphere. One contains DPD at low pH because DPD is air sensitive at the reaction pH of 6.3, and a separate pH buffer to fix the reaction pH at 6.3. The device also consumes considerable quantities of reagents. This results in a considerable operating expense and significant operator time to replace reagent containers. The peristaltic pump tubing requires periodic replacement, requiring additional operator time. Furthermore, an (optional) on-line filter is preferred to "prolong the life of the meter".

U.S. Pat. No. 5,132,096 is an early example to methods of monitoring water treatment performance by resolving optical voltage analogs using a tracer metal added to the reagent.

U.S. Pat. No. 5,242,602 discloses a system for analysing aqueous systems using spectroscopic and pattern recognition techniques based on pre-calibrated databases U.S. Pat. No. 5,925,572 discloses a continuous spectrophotometric pH sensor for sea water. It uses a flow through cell with three wavelength channels. A calibration routine is carried out every 15 minutes.

U.S. application 2002/0054828 discloses a waste water analysis unit immersed in the water, using removable reagent cartridges.

U.S. Pat. No. 6,627,450 discloses a method of measuring free chlorine content which provides an inline cartridge of a solid reagent. It is concerned with a total chlorine detection system using a combination of an iodide salt and a proton donating compound such as bicarbonate without lowering the pH of the sample.

It is an object of this invention to provide a reliable cost effective online chemical analysis instrument.

It is also an object of this invention to provide a system which is able to use an air sensitive reagent.

SUMMARY

To this end, the present invention provides a method of analysing a liquid sample to determine the presence of a target chemical, in which a sample is added to a measurement cell of known volume and a reagent is incrementally added to the cell until a detectable change is observed, the improvement comprising the incorporation in the reagent of a known concentration of a reference compound that does not take part in the reaction and measuring the concentration of the reference compound to determine the amount of reagent added.

One of the contributors to the high cost of other available on-line analysers which automate standard methods, is accurate volume dispensing means. In knowing the volume of reagent added and the cell volume, the final concentrations of reagents can be determined. The approach in this invention is to use a reference compound to deduce the final concentration and the volume dispensed can be determined retrospectively or regulated by monitoring the level of reference.

Internal standards have been used in chemical analysis, where a compound is added in a known concentration to the sample and undergoes the same sample preparation and reaction steps as the analyte. The resultant detected signal for the target chemical is then calibrated against the reacted product signal of the known concentration of internal standard. In this invention a reference compound is added to the reagent solution, rather than directly to the sample to be analysed, in a known proportion to the other chemicals in the reagent solution and does not undergo any subsequent chemical changes. The purpose of the reference compound is purely as an indicator of how much reagent solution has been added. Reagent solution is added to the sample in the measurement cell and the final concentration of the reference compound is measured via its absorbance. The concentrations of other reagent chemicals in the cell after reagent addition can then be determined relative to the reference compound concentration. Knowing the cell volume and the concentration then allows calculation of the volume dispensed, which is very useful for various diagnostic purposes.

Throughout this specification, the term "reagent" includes any solution added to the sample fluid regardless of function. The term includes a solution of a substance which may react with the analyte of interest to produce a reaction product with a measurable property substantially different from the properties of both the reagent and sample fluids. The term also includes substances which do not react with the analyte (target chemical), but are added for a variety of purposes, including substances which: fix variables such as pH and ionic strength; suppress interferences; preserve components; act as a reference compound and the like. A single reagent may contain any number of such substances. Alternatively, it will be appreciated that some embodiments of the present invention provide for the addition of any number of separate reagents which may be added simultaneously or sequentially to the sample. The term also includes titrants, where incremental volumes of a reagent are added successively to the sample until an end-point is reached.

In another aspect, this invention provides a simple means of delivering a volume of reagent into a measurement cell incorporating a first port to introduce sample fluid; a second port to allow injection of fluid reagent; and a third port to allow expulsion of sample and sample/reagent mixtures to waste which includes a compressible reservoir of reagent which is positioned within a second preferably rigid container, and is surrounded by a fluid which substantially fills the space between said reservoir and the inside wall of said container and means for generating a pressure differential between said fluid and said reservoir to effect partial collapse of said reservoir in order to inject reagent into said measurement cell. The fluid surrounding the reservoir may be a liquid or a gas.

The sample delivery means may comprise a T-piece outlet from a conduit to allow a portion of a flowing stream of sample in the conduit to enter the measurement cell. The sample may flow continuously through the measurement cell or a valve (for example a solenoid valve) may be employed to allow sample to flow into the measurement cell and to stop the flow of sample after the measurement cell has been flushed with fresh sample fluid. Alternatively, the sample delivery means may comprise a peristaltic, piston, centrifugal, piezo or any type of pump which actively pumps sample into the measurement cell from a container or flowing stream. The sample/reagent mixture may be expelled to waste or back into the flowing stream from which the sample came.

The means of compression of the compressible reagent reservoir involves pressurisation of a gas or liquid surrounding the compressible reservoir, including but not limited to, exposing the surrounding fluid or gas to a higher pressure or temperature than that of the reagent reservoir. Thus pressurisation of the reagent reservoir is a result of pressurisation of the surrounding fluid, as distinct from the operation of a peristaltic pump which causes a pumping action by direct mechanical compression of a compressible tube connected to a reservoir of reagent. The pressurisation creates a pressure differential when the reservoir output is connected to a different pressure than that of the surrounding fluid. The compressible reagent reservoir may also serve to protect the reagent from air and/or light and may for example be a bag constructed from a suitable polymer film or a polymer/metal film composite.

Injection of the reagent through pressurisation of a fluid surrounding a compressible reagent reservoir may be accomplished by several means. The container surrounding the reagent reservoir may be pressurised with a gas. Preferably, the container of gas and reagent operates in conjunction with a solenoid valve which can be activated to deliver reagent into the sample contained within the measurement cell. The delivery of reagent into the sample when the solenoid valve is open may be continuous until the valve is closed. Alternatively, the delivery of reagent may be an incremental volume under the control of an elastic diaphragm of defined volume. The reagent is preferably separated from the gas by a compressible bag in order to prevent variation in the concentration of the reagent caused by evaporation and condensation of the reagent fluid within the container.

Alternatively, the container surrounding the reagent reservoir may be filled with a liquid. The surrounding fluid may be pressurised to cause injection of the reagent by compression of the reagent reservoir. In one embodiment of the invention, the surrounding fluid may be pressurised by exposure to a high pressure line, such as the flow line from which the sample is taken. In another embodiment the surrounding fluid may be pressurised by a pumping device such as a centrifugal pump.

In yet a further aspect of this invention, there is provided a chemical analyser in which a single mechanism introduces a sample, adds reagent and cleans and flushes the measurement cell. The analyser incorporates a longitudinal chamber having a number of fluid inlets for sample and reagent and an outlet for the measured sample/reagent mixture, a detector being located in said chamber between the inlets and said outlet and a piston movable in said chamber carrying a series of seals such that movement of the piston sequentially opens the inlets and expels the sample/reagent mixture. The inlets and outlets preferably also include one way valves responsive to changes in pressure created by movement of the piston. The reagent delivery means of this invention is used in association with this mechanism.

The sensing means and associated electronic circuitry may comprise an optical system which can operate in conjunction with other types of sensors such as electrochemical sensors. Alternatively, any combination of sensing systems may be employed. Suitably, an optical sensing system comprises an emitter capable of emitting light of more than one wavelength; and a detector capable of responding to light of different wavelengths. The optical or chemical sensors can detect the presence of a reaction product between the reagent and the target chemical (analyte) to be measured. In a titration the optical sensor measures the quantity of the reaction product by a characteristic light absorption. A similar absorption measurement of the reference compound provides an indication of the amount of reagent added.

One particular application of this invention is in analysing water in air conditioning cooling towers and swimming pools. Optical sensing of chlorine as part of a control system for managing salt and chlorine levels in swimming pools with a salt chlorinator has not previously been provided. This enables a control system for the recirculating pumps and salt chlorinator to use the assessment of chlorine levels as part of the control program and provide more economical use of the pumps and salt chlorinator with consequent energy savings.

BRIEF DESCRIPTION OF THE DRAWINGS

Various preferred embodiments of the invention will now be described with reference to the drawings.

DETAILED DESCRIPTION

Figure 1:
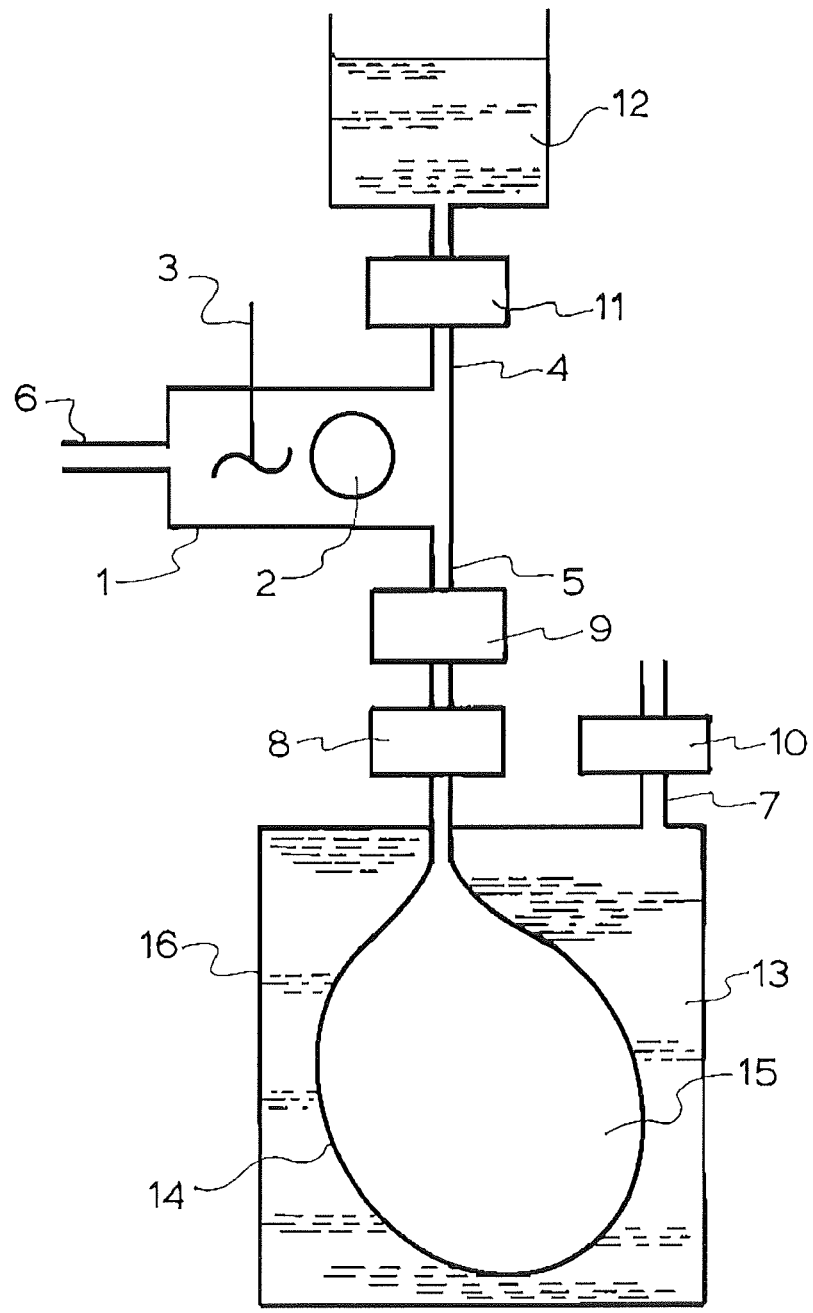
FIG. 1 is a block diagram of a basic configuration of chemical analyser for carrying out the method of the invention.
Figure 3A:
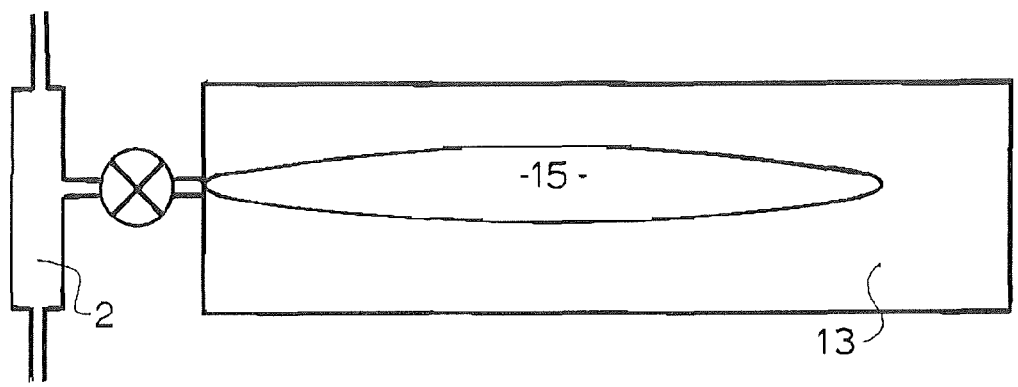
FIG. 3 shows three alternative configurations of the reagent dispenser.
Figure 3B:
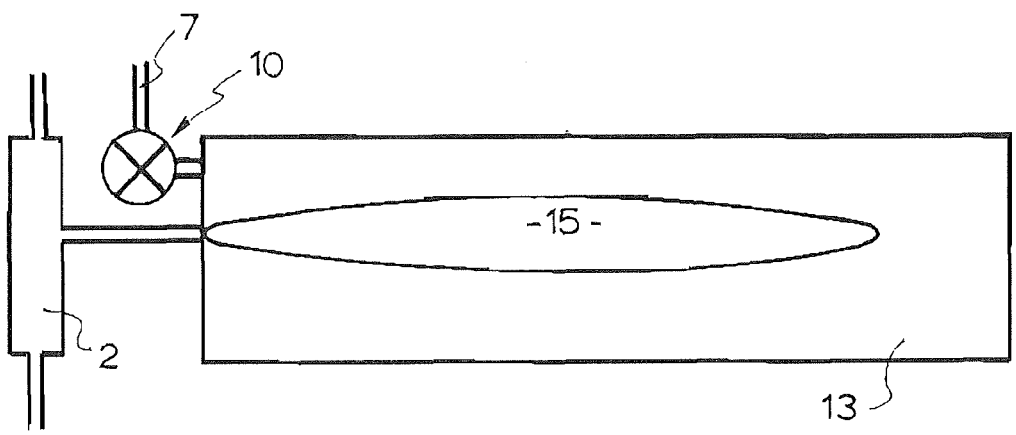
Figure 3C:
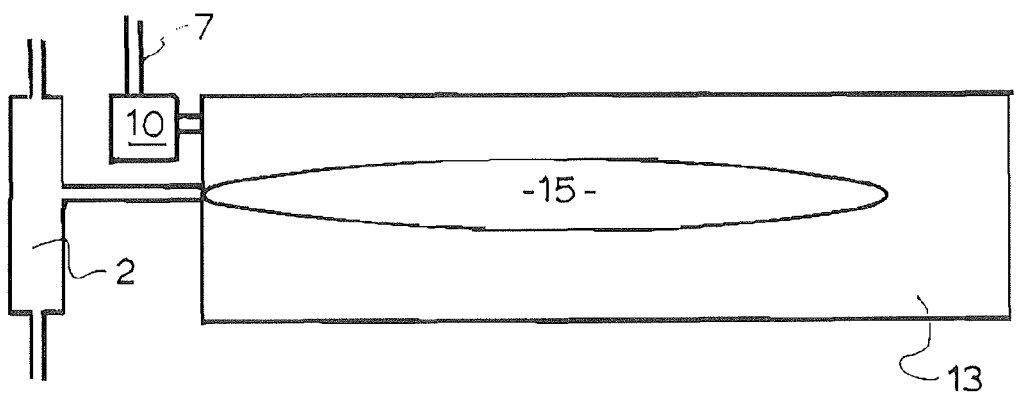

Referring to FIG. 1, measurement cell 1 incorporates detector 2 and mixer system 3, and is connected to sample fluid 12 by sample fluid line 4. The introduction of sample 12 into measurement cell 1 can be controlled by control means 11, which may be a pump, or any type of valve. Waste fluid line 6 allows excess sample 12, or mixtures of sample fluid 12 and reagent fluid 15 to be expelled to waste. Reagent 15 is connected to measurement cell 1 by reagent fluid line 5. The injection of reagent 15 into measurement cell 1 can be controlled by control means 9, which may be any type of pump or valve. The flow of reagent 15 into measurement cell 1 can be regulated by injection mechanism 8, which may include a flow restrictor such as a filter; a ball valve; or a diaphragm. Reagent 15 is contained in collapsible reagent reservoir 14, which may be a bag of flexible material and which is positioned inside rigid container 16, and surrounded by fluid 13 which may be a gas or a liquid. Pressure on fluid 13 causes the partial collapse of collapsible reservoir 14, and subsequent injection of reagent 15 into measurement cell 1. As shown in FIG. 3A, this pressurisation may be constant and the valve controls the injection of reagent. Pressurisation of fluid 13 may be effected by the admission of fluid through fluid line 7, and controlled by control means 10, which may be any type of valve as shown in FIG. 3B or pump as shown in FIG. 3C.

Figure 2:
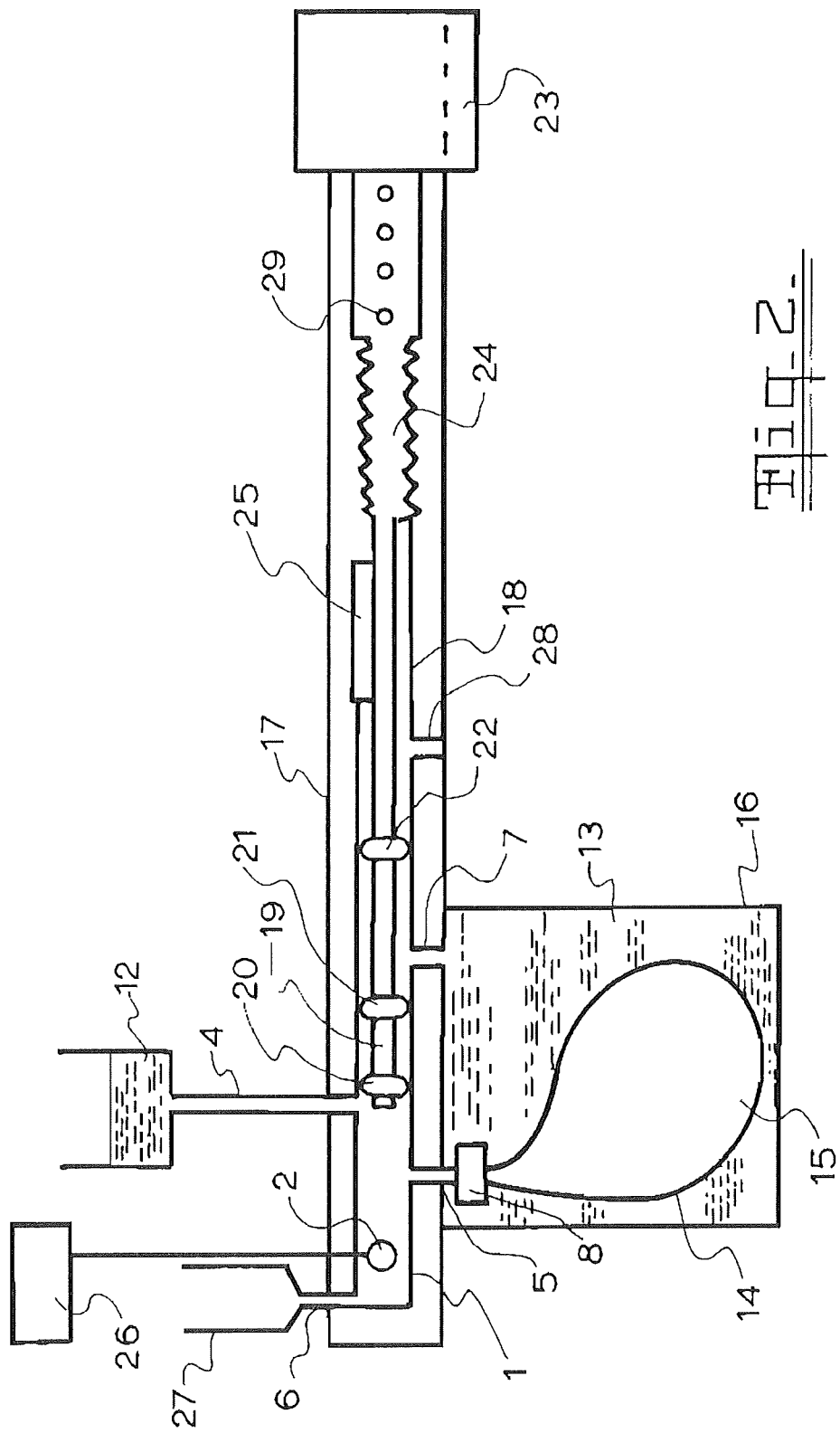
FIG. 2 is a more detailed counterpart of the block diagram of FIG. 1 which refers to a preferred embodiment of the invention.

FIG. 2 depicts a more developed counterpart of FIG. 1, and illustrates a preferred embodiment of the invention.

Referring to FIG. 2, analyser body 17 incorporates longitudinal chamber 18 which terminates in measurement cell 1. Piston 19 incorporates seals 20, 21 and 22, and is driven forwards and backwards by motor 23 (which may be a stepper motor) via threaded drive 24. Piston 19 is prevented from turning by keyway 25. Sample 12 is delivered through sample line 4 into chamber 18 to either flush measurement cell 1, or pressurise fluid 13 in container 16 by flowing through fluid line 7. The pressurisation of fluid 13 causes the partial collapse of collapsible reservoir 14 so that reagent 15 may flow into injector mechanism 8 and thence into measurement cell 1 via reagent fluid line 5. Injector mechanism 8 can be a flow restrictor known in the art such as a filter, a ball valve, or diaphragm. Measurement cell 1 incorporates detector 2 which outputs to analyser circuit 26. The contents of measurement cell 1 can be expelled to waste through waste fluid line 6 and into reservoir 27. Fluid line 28 vents fluid 13 so that fluid 13 is under atmospheric pressure at the beginning of a cycle. This overcomes pressure increases in fluid 13 when the analyser is not operating, which can be caused by thermal expansion of fluid 13. The movement of piston 19 in conjunction with seals 20, 21 and 22 acts as a system of sliding valves, which close or open fluid lines 4, 5, 7 according to particular steps in the measurement cycle. Piston 19 may be stopped at any required position by position sensor 29. Alternatively, a stepper motor can be used to determine the position and the detector 2 may also provide additional positioning information.

A first embodiment of the invention utilises a single mechanism for the functions of: sampling from a flow line, pressurising the fluid around the compressible reagent bag to effect injection, mixing of the reagent/sample, cleaning of the measurement cell, and flushing out of the analysed sample.

In a preferred application, the analyser of this invention is used to measure the chlorine content of water particularly in air conditioning cooling towers and swimming pools.

Figure 4A:
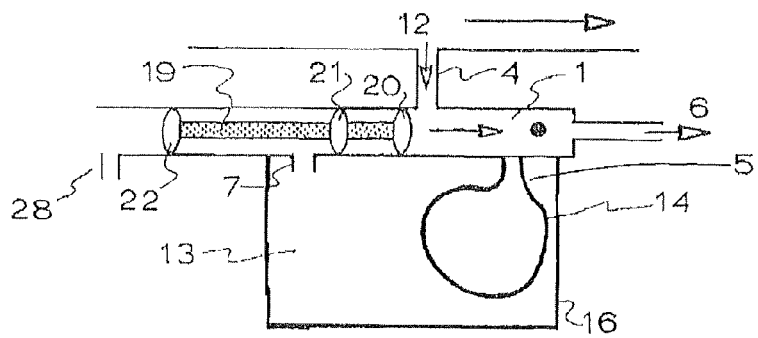
FIG. 4 schematically shows piston positions corresponding to particular steps which comprise a measurement cycle for the preferred embodiment of FIG. 2.

The analyser is attached directly to the pool pump line which is to be sampled. The functions required are performed via a single linear drive mechanism which slides a piston with o-ring seals back and forward through the chamber. The reagent solution is contained inside a compressible reservoir which is in turn contained inside a vessel filled with water. The reagent reservoir and its outer container are structured as an easily replaceable single unit, and each reagent container may provide more than 6 months worth of analyses. The material of the reservoir wall prevents diffusion and also further serves to further exclude oxygen from the reagent. In FIG. 4A the piston is in the flush position where the tube is exposed to the pressurised pool line and new sample is flushed through the tube. The piston is then driven forward to the inject position (FIG. 4B) where the water surrounding the reagent reservoir is exposed to the pool line pressure. This pressurises the reagent reservoir which compresses and causes a reagent injection into the measurement tube.

After injection the piston is then driven to the end of the tube (FIG. 4C), thereby forcing the contents of the water sample plus injected reagent into the mixing region at the end of the chamber. It is then drawn back to the measurement position and in doing so sucks the reagent sample mixture back into the chamber. The squeezing of the solution into and back out of the mixing chamber causes a mixing action.

In the measure position (FIG. 4D) the optical measurement is performed through the walls of the measurement tube.

Thus this single mechanism performs the functions of flushing of previous sample/reagent mixture; introduction of fresh sample, reagent injection/pumping and mixing. It also performs the additional function of cleaning by wiping the walls of the measurement cell.

FIG. 4 also shows the positions of piston 19, corresponding to particular steps in the measurement cycle. FIG. 4A, corresponding to the sample flush step, shows piston 19 withdrawn to allow sample 12 to flush measurement cell 1 with new sample. Detector 2 records a baseline value. Excess sample 12 is expelled through fluid waste line 6 and into reservoir 27. Fluid line 7 is closed by seals 21 and 22, thus preventing the injection of reagent 15 into measurement cell 1. Vent fluid line 28 is closed to fluid 13 by seal 22.

Figure 4B:
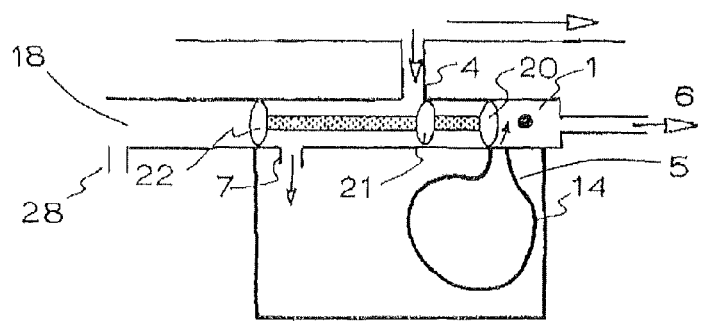

FIG. 4B, corresponding to the reagent injection step, shows the position of piston 19 for the injection of reagent 15 into measurement cell 1. Sample fluid line 4 is in fluid communication with fluid line 7, so that pressure from sample 12 is transmitted to fluid 13 in container 16. This causes collapsible reservoir 14 to partially collapse, thus injecting reagent 15 into measurement cell 1 via line 5. The volume injected is regulated by the time spent in the injection position and injection mechanism 8, which may allow continuous injection as with a flow restrictor, or a substantially fixed volume from an incremental injector such as a diaphragm. Sample fluid line 4 is closed to measurement cell 1 by seal 20. Vent fluid line 28 remains closed to fluid 13 by seal 22.

Figure 4C:
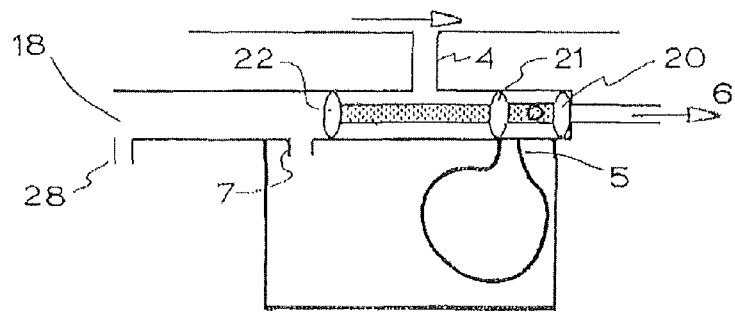

FIG. 4C, corresponding to a park or mixing step, shows piston 19 driven fully forward to the end of measurement cell 1. In this step there is no flow of sample 12, nor reagent 15 because seals 20, 21 and 22 block fluid communication between sample line 4, and fluid lines 6, and 7. However, fluid lines 7 and 28 are in fluid communication, so that fluid 13 pressure can be reduced to atmospheric by venting excess fluid or gas through fluid line 28.

The contents of measurement cell 1, comprising a mixture of sample 12 and reagent 15, are expelled into fluid line 6 and reservoir 27. This step is used when the apparatus is not operating between cycles. Alternatively, it is used as a transient step for mixing sample fluid 12 with reagent 15.

Figure 4D:
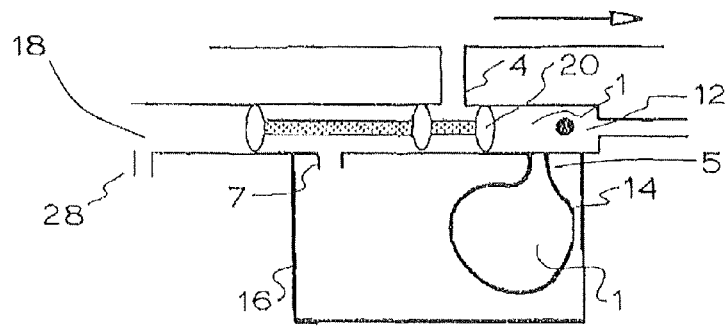

FIG. 4d, corresponding to the measurement step, shows piston 19 withdrawn to a position which defines the measurement cell volume. The withdrawal of piston 19 pulls back the mixture of sample 12 and reagent fluid 15 from reservoir 27 into measurement cell 1. This causes turbulent mixing of sample 12 and reagent 15. If necessary, piston 19 may move backwards and forwards between the park and measurement positions several times to effect complete mixing. A feedback system from the reference absorbance reading may be used to control the volume. Seal 20 prevents the injection of reagent 15 into measurement cell 1. Upon the withdrawal of piston 19 from the park position, seal 20 cleans the walls of measurement cell 1. Detector 2 records a value proportional to the analyte (target chemical) of interest.

At the completion of the cycle, piston 19 can return to the park position, or continue cycling by returning to the flush step.

Figure 5:
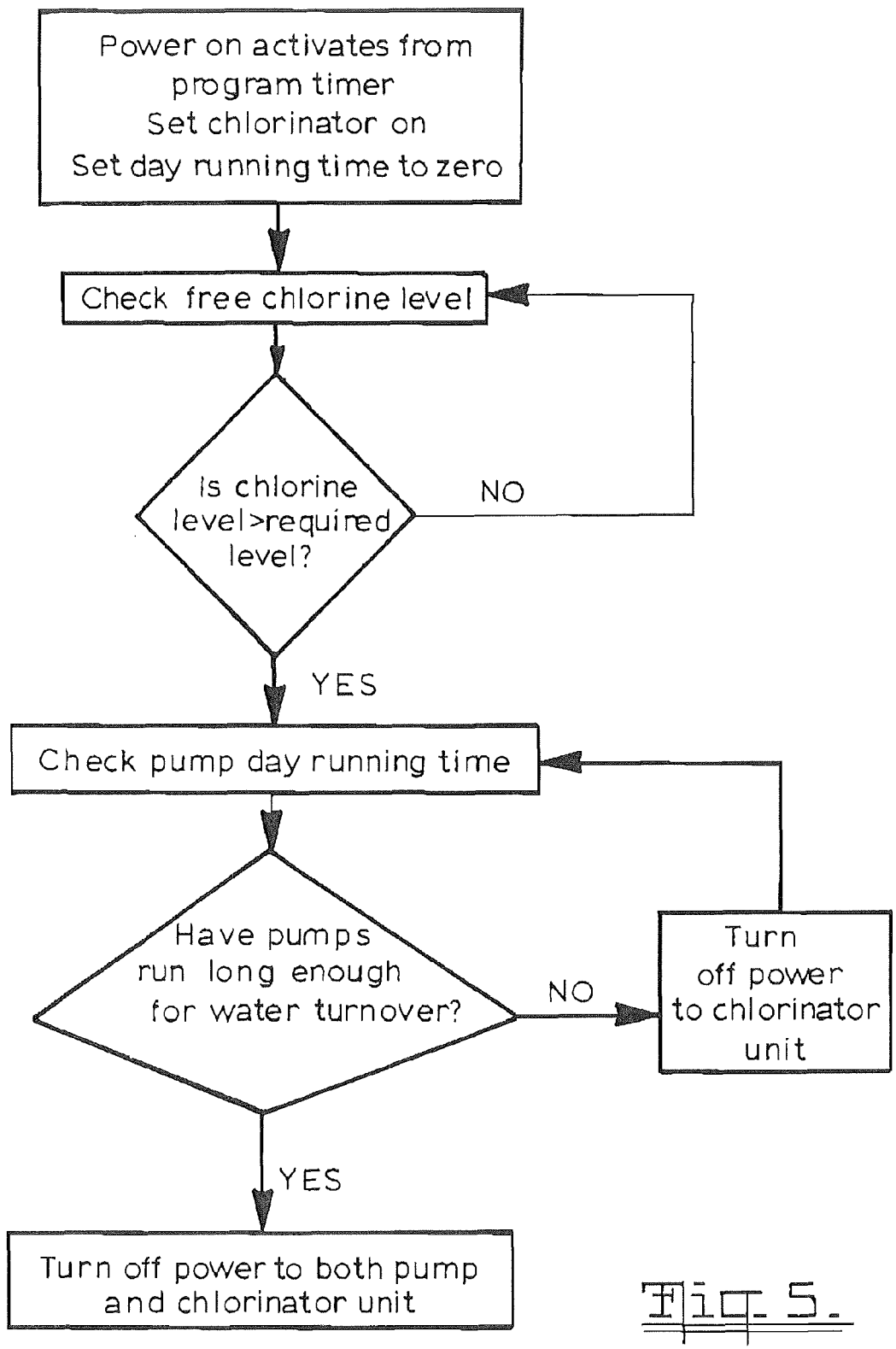
FIG. 5 is a flow chart of operation relating to a particular example of analysis.

An additional aspect of the invention in relation to application to analysis of chlorine in swimming pools is utilisation of the measurement result as feedback for a control system which controls the power to the re-circulating pumps and/or salt chlorinator units. Such a control system can result in significant energy savings. A flow diagram for the logic of such a control system is shown in FIG. 5.

Figure 6:
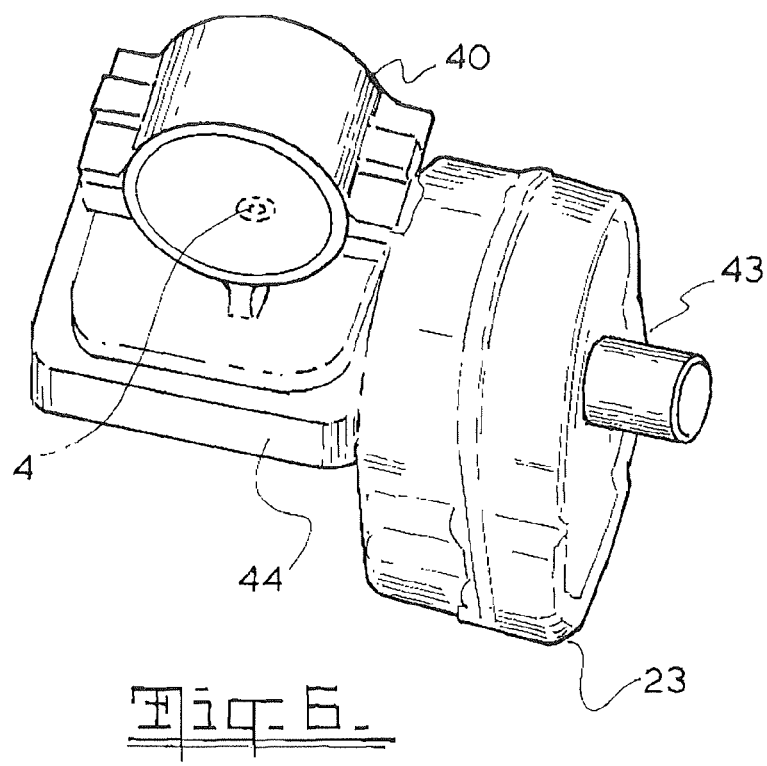
FIG. 6 is an isometric view of an embodiment of the invention without the reagent container.
Figure 7:
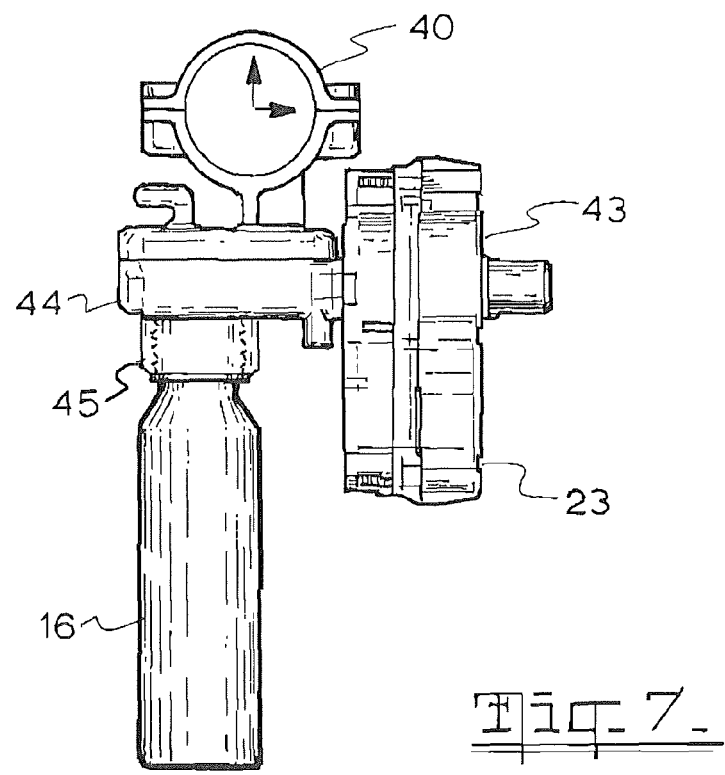
FIG. 7 is a side view of the embodiment of FIG. 6 with the reagent container.
Figure 8:
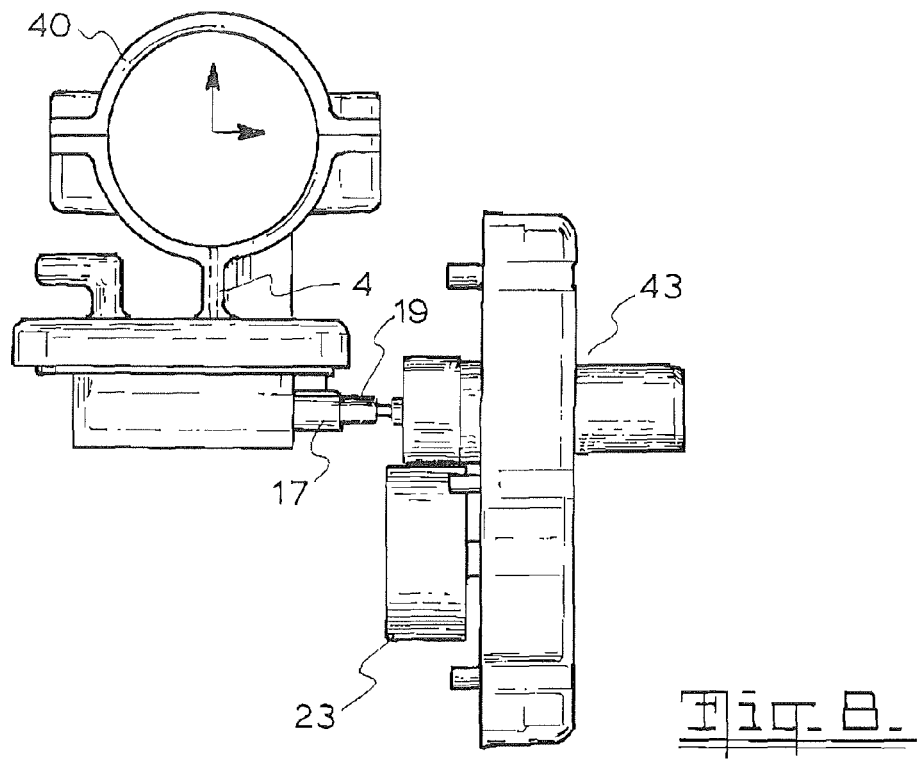
FIG. 8 is an exposed side view of the embodiment of FIG. 6 without the reagent container.
Figure 9:
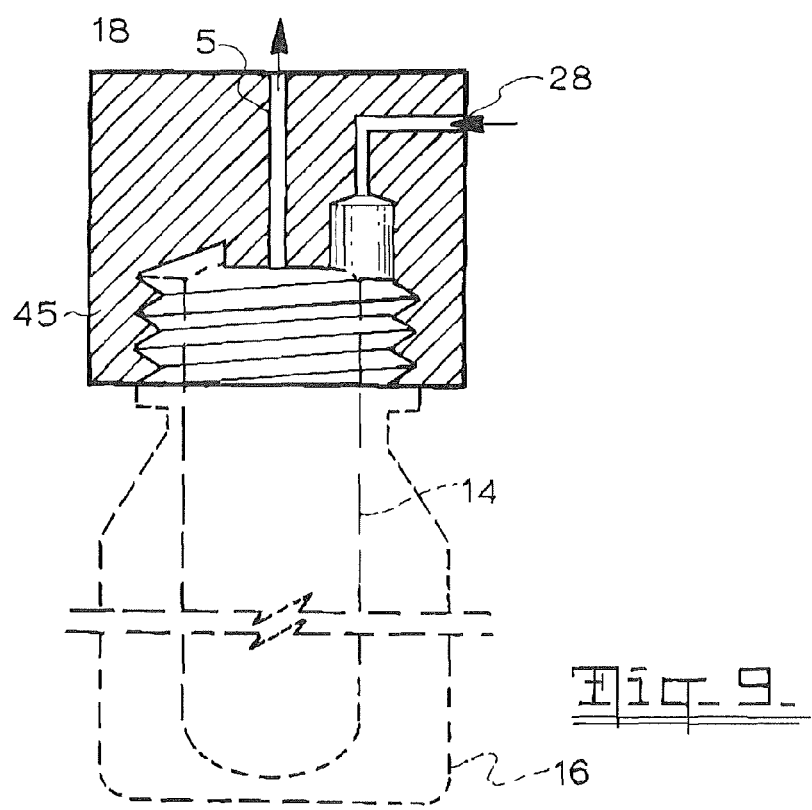
FIG. 9 is a detail of the attachment of the reagent container as shown in FIG. 7.

The embodiment of FIGS. 6 to 8 is adapted to be fitted to the return water conduit of a swimming pool. A sample hole is drilled in the water conduit and this is aligned with the sample inlet 4 which is incorporated in the clamp 40 that holds the analyser to the pool return pipe. The motor 23 and its associated gear 43 drives the piston 19 within the barrel or analyser body 17 as schematically shown in FIGS. 2 to 4. The reagent container 16 is screw threaded to the cover 44 which encloses the barrel 17. The cover 44 incorporates the screw threaded housing 45 to which the container 16 is coupled. The container could be secured by a snap-on or clip system instead of a screw thread. As shown in FIG. 9, the reagent container 14 is connected to reagent line 5. Venting of the content of container 16 occurs through venting line 28. The inlet of housing 45 and the neck of container 16 are shaped to allow the reagent dispenser to be self priming.

The preferred optical system uses a light emitting diode (LED) as the light source with two or more wavelengths. The use of multiple wavelengths allows solution of simultaneous equations for several compounds in the solution. The reference compound is generally chosen such that its main absorbance occurs at a different wavelength from the reaction product produced. For example, a blue reference compound would be used with reactions which produce a red product.

The purpose of the reference compound is purely as an indicator of how much reagent has been added. Reagent is added to the sample in the measurement cell and the final concentration of the reference compound is measured via its absorbance. The concentrations of other reagent chemicals in the cell after reagent addition can then be determined relative to the reference compound concentration. Knowing the cell volume and the concentration then allows calculation of the actual volume dispensed, which is very useful for various diagnostic purposes.

Three dispensing cases which can be encountered in performing an analysis are:

1) The reactive chemical component of the reagent is needed in excess. In this situation accurate dispensing is not required as it is only necessary to ensure at least a minimum volume is dispensed to ensure a high enough concentration of reactive chemical. In this case the reference compound is used for diagnostic purposes, such as confirmation that the reactive chemical has actually been added and in sufficient amount. This provides an indication that the measurement is actually reliable.

2) Titrations. In performing a titration the reagent is added to determine an end point which is used to calculate the concentration of target chemical. The reagent is added either in successive increments or continuously. In the sequential method an aliquot is dispensed, the solution mixed, and a measurement made. The process is repeated a number of times to produce measured points through which a curve can be fitted and the end point determined. It is necessary to know accurately what the concentrations of reactive chemical added are at each measurement point, and the reference compound performs this function without having to rely on accurate volumes being dispensed.

In some embodiments, a titration can also be performed via continuous addition of reagent. The absorbance transient is measured at all wavelengths. At the end point indicated by the absorption wavelengths of the target chemical, the absorption of the reference compound at this same point in the transient provides a measure of the amount of reactive chemical which has been added.

3) Reactions dependent on adding specific volumes of reagents. In this case the reference compound provides diagnostics and provides information on the actual volume which has been added. Reactions where the volume injected is critical, are addressed by an additional metered dose mechanism incorporated in the system.

Another important aspect of the invention is reducing the amount of reactive chemical needed, and hence reducing running costs of consumables. Reagent consumption in usage is reduced via:

Scaling down of physical dimensions

Increasing concentrations of compounds in the reagent

Where possible combining multiple compounds in the one reagent solution

The dimensions of the system have been reduced relative to most typical systems. The cell volume in a preferred embodiment is of the order of 100 microlitres, whereas most conventional systems use millilitre volumes. Ultimately the invention could be scaled down further to employ microfluidic technologies, but in the current system these dimensions have been chosen to fit in with readily available robust plastic moulding procedures and other readily available components. The volume of reagent dispensed in one preferred embodiment is typically of the order of one microlitre.

Those skilled in the art will realise that this invention provides a significant improvement in the reliability and cost of online analysis. The analyser is reliable and inexpensive and will improve the control of chemical use in chlorinated water systems such as swimming pools.

The ability to calculate the volume dispensed is useful in diagnostic analysis of the performance of the analyser itself. The absence of an absorbance reading of the reference may indicate mechanical, detector or electronics malfunction, blockage of a fluid line or exhaustion of reagent. A reference absorbance reading may be compared to previous readings to provide an alert of abnormal behavior of the system to allow the process control to be stopped in real time.

The simplified construction with one moving part reduces the cost of the analyser and improves reliability. The use of small volumes also reduces operating costs. At a sampling rate of 1 micro litre every 15 minutes, 35 ml of reagent will last about 12 months.

Those skilled in the art will also realise that this invention can be implemented in embodiments other than those described without departing from the core teachings of this invention.

The invention claimed is:

1. An on-line chemical analyzer for analyzing sample portions of fluid taken from a line, the on-line chemical analyzer comprising:
   a longitudinal chamber incorporating:
      a sample inlet port to allow entry of a sample fluid into the longitudinal chamber,
      a reagent inlet port to allow a reagent fluid into the longitudinal chamber, and
      an outlet port in fluid communication with the sample inlet port and the reagent inlet port;
   a piston moveable in the longitudinal chamber, wherein a series of seals is mounted on the piston such that movement of the piston sequentially allows fluid communication along the longitudinal chamber;
   a measurement cell located in the longitudinal chamber to receive the sample fluid, the reagent fluid, or a mixture of sample and reagent;
   a detector located in or adjacent to the measurement cell;
   a substantially rigid container in fluid communication with the longitudinal chamber;
   a compressible reagent reservoir positioned within the substantially rigid container, wherein the compressible reagent reservoir is in fluid communication with the reagent inlet port; and
   a piston controller to position the series of seals within the longitudinal chamber to subsequently allow fluid communication along the longitudinal chamber;
   wherein the piston controller moves the piston so that fluid communication is established from the longitudinal chamber to the substantially rigid container to pressurize the compressible reagent reservoir and cause injection of the reagent fluid into the measurement cell.

2. An on-line chemical analyzer as claimed in claim 1, wherein the amount of the reagent fluid injected into the measurement cell is controlled via the length of time the compressible reagent reservoir is under pressurization.

3. An on-line chemical analyzer for analyzing sample portions of fluid taken from a line, the on-line chemical analyzer comprising:
   a storage container having a compressible reservoir and a storage area around the compressible reservoir;
   a longitudinal chamber having:
      a first fluid inlet configured to provide a sample fluid,
      a second fluid inlet configured to receive a reagent fluid from the compressible reservoir,
      a first fluid outlet configured to dispense fluid to the storage area to thereby place pressure on the compressible reservoir,
      an outlet port, and
      a mixing area between the first fluid inlet and the outlet port; and
   a piston movable in the longitudinal chamber and having a plurality of spaced apart seals mounted thereon, the piston having at least two positions in which interactions of the seals with the longitudinal chamber create different fluid pathways, the at least two positions including:
      a first position in which the first fluid inlet is (a) in fluid communication with the mixing area, and (b) isolated from the first fluid outlet; and
      a second position in which the first fluid inlet is (a) isolated from the mixing area and (b) in fluid communication with the first fluid outlet, wherein pressurized sample fluid can move from the first fluid inlet into the storage area to constrict the compressible reservoir and force reagent fluid into the mixing area.

4. The on-line chemical analyzer as claimed in claim 3, wherein the piston is configured to move sequentially through the first position and the second position to thereby respectively (a) inject sample fluid into the mixing area but not the storage area, and (b) inject sample fluid into the storage area, but not the mixing area, to compress the reservoir and inject reagent fluid into the mixing area.

5. The on-line chemical analyzer as claimed in claim 3, wherein the piston has a third position in which the first fluid inlet is isolated from the mixing area and from the first fluid outlet.

6. The on-line chemical analyzer as claimed in claim 5, wherein the piston is configured to move sequentially through the first, second and third positions, wherein a transition from the second position to the third position isolates the first and second fluid inlets from the mixing area and expels collected fluid in the mixing area through the outlet port.

7. The on-line chemical analyzer as claimed in claim 5, wherein the piston has a fourth position in which the first fluid inlet is isolated from the mixing area and from the first fluid outlet port, and movement of the piston from the third position to the fourth position draws fluid into the mixing area from the outlet port.

8. The on-line chemical analyzer as claimed in claim 3, further comprising an external reservoir connected to the outlet port and downstream from the longitudinal chamber.

9. The on-line chemical analyzer as claimed in claim 8, further comprising a detector located in or adjacent to the mixing area.

10. An on-line chemical analyzer as claimed in claim 9, wherein the detector is an optical absorbance detector.

11. An on-line chemical analyzer as claimed in claim 3, wherein the second fluid inlet is associated with an injection control mechanism that includes one of a filter, a valve, or a diaphragm.

12. An on-line chemical analyzer as claimed in claim 3, wherein the longitudinal chamber is in fluid communication with a vent fluid line.

13. An on-line chemical analyzer as claimed in claim 3, wherein the compressible reservoir comprises a wall material that excludes oxygen from the reagent fluid.

14. An on-line chemical analyzer as claimed in claim 3, wherein the outlet port is configured to expel the sample fluid or a mixture of the sample fluid and the reagent fluid.

15. An on-line chemical analyzer as claimed in claim 3, further comprising a piston controller that positions the piston.

16. An on-line chemical analyzer as claimed in claim 3, wherein an amount of the reagent fluid injected into the mixing area is controlled via the length of time the compressible reservoir is under pressurization.

17. An on-line chemical analyzer as claimed in claim 3, further comprising a detector configured to detect an amount of the reagent fluid injected into the mixing area by measuring a concentration of a reference compound present in a combination of reagent fluid and sample fluid within the mixing area.

* * * * *